(12) United States Patent
Schneider et al.

(10) Patent No.: US 6,281,244 B1
(45) Date of Patent: Aug. 28, 2001

(54) THERAPEUTIC USE FOR GLYCINE

(75) Inventors: Heinz Schneider, Cordast (CH); Ronald G. Thurman, Chapel Hill, NC (US); Nigel Scott Cook, Bretzwil (CH)

(73) Assignee: Novartis Nutrition AG, Bern (CH)

( * ) Notice: Subject to any disclaimer, the term of this patent is extended or adjusted under 35 U.S.C. 154(b) by 0 days.

(21) Appl. No.: 09/080,859

(22) Filed: May 18, 1998

Related U.S. Application Data

(60) Provisional application No. 60/048,735, filed on Jun. 5, 1997.

(51) Int. Cl.$^7$ .......................... A61K 31/195; A61K 38/13
(52) U.S. Cl. ............................... 514/553; 514/9; 514/14; 514/554; 530/317; 530/327; 560/19
(58) Field of Search .............................. 514/9, 14, 553, 514/554; 530/317, 327; 560/19

(56) References Cited

U.S. PATENT DOCUMENTS

| | | | |
|---|---|---|---|
| 5,026,728 | 6/1991 | Kendall et al. | 514/561 |
| 5,221,668 * | 6/1993 | Henningfield et al. | 514/23 |
| 5,290,538 * | 3/1994 | Bertermann | 424/10 |
| 5,349,060 * | 9/1994 | Kao et al. | 540/346 |
| 5,576,351 * | 11/1996 | Yoshimura et al. | 514/546 |
| 6,096,785 * | 8/2000 | Schneider et al. | 514/561 |

FOREIGN PATENT DOCUMENTS

| | | |
|---|---|---|
| 295765 | 11/1991 | (NL) . |
| 93/15736 | 8/1993 | (WO) . |

OTHER PUBLICATIONS

Den Butter, et al., "Effect of Glycine in Dog and Rat Liver Transplantation" Transplantation 1993, 56, 817–22.*
DeNicola, L. et al., Journal of Clinical Investigation, vol. 92, pp. 1859–1865 (1993).
Saint Marie, R. L. et al., The Journal of Comparative Neurology, vol. 279, pp. 382–396 (1989).
Watson, A.J.M. et al., Gastroenterology, vol. 94, pp. 863–869 (1988).
Jain, P. et al., Indian Jouranl of Experimental Biology, vol. 27, Mar. 1989, pp. 292–293 (1989).
Adler, L.B.A. et al., Scand. J. Immunol., vol. 44, pp. 585–591 (1996).
Gautreau, C. et al., Transplantation, vol. 60, pp. 903–907 (1995).
AASLD Abstracts, vol. 24 (4, Part. 2), p. 434A (1996).
Dowd, L.A. et al., J. Neurochem., vol. 67(2), pp. 508–516 (1996).
Chemical Abstracts, vol. 125, No. 13, 158061e (1996).
Chemical Abstracts, vol. 91, 209130r (1979).
Derwent Abstracts, 94–295291/37 (1994), DE 4309339–A1.

* cited by examiner

*Primary Examiner*—Karen Cochrane Carlson
*Assistant Examiner*—Anish Gupta
(74) *Attorney, Agent, or Firm*—Hesna J. Pfeiffer

(57) ABSTRACT

Glycine is indicated to prevent or treat acute or chronic graft rejection, optionally in combination with an immunosuppressant or an immunomodulating agent.

4 Claims, No Drawings

THERAPEUTIC USE FOR GLYCINE

This application claims benefit of provisional application 60/048,735, filed Jun. 5,1997.

The present invention relates to a new use of glycine alone or in combination with other therapeutic agents.

It is known to use a medicament or nutritional formulation comprising glycine, alanine or serine as an active ingredient to minimize or prevent the metabolic effects of a wide range of disease states or conditions induced by elevated tumor necrosis factor (TNF) levels.

It has now been found that glycine is indicated to prevent or treat acute or chronic graft rejection. Thus the invention provides:

1.1. A method of preventing or treating non TNF-induced transplant rejection in a recipient of organ or tissue transplant, e.g. heart, lung, combined heart-lung, trachea, bowel, liver, kidney or pancreatic transplants, comprising the step of administering to said recipient a therapeutically effective amount of glycine, in free form or in pharmaceutically acceptable salt form;

1.2. A method of preventing or treating manifestations of chronic rejection in a recipient of organ or tissue transplant, e.g. heart, lung, combined heart-lung, trachea, liver, bowel, kidney or pancreatic transplants, comprising the step of administering to said recipient a therapeutically effective amount of glycine, in free form or in pharmaceutically acceptable salt form;

Chronic rejection is considered as a multifactorial process in which not only the immune reaction towards the graft but also the response of the blood vessel wall in the grafted organ to injury plays a role. The variant of chronic rejection with the worst prognosis is an arteriosclerosis-like alteration, also called transplant vasculopathy graft vessel disease. This vascular lesion is characterized by migration and proliferation of smooth muscle cells. It appears to progress also through repetitive endothelial injury induced amongst others by host antibody or antigen-antibody complexes, through intimal proliferation and thickening, smooth muscle cell hypertrophy repair, and finally to gradual luminal obliteration. Also so-called non-immunological factors like hypertension, hyperlipidemia, hypercholesterolemia etc. play a role.

2. A pharmaceutical composition or nutritional formulation for use in any method as defined hereinabove comprising glycine, in free form or in pharmaceutically acceptable salt form, together with a pharmaceutically acceptable diluent or carrier therefor.

In a series of further specific or alternative embodiments, the present invention also provides:

3.1. Use of glycine, in free form or in pharmaceutically acceptable salt form, in combination with an immunosuppressant or immunomodulating agent or a mixture thereof, in a method as defined hereinafter under 1.1 or 1.2;

3.2. Use of glycine, in free form or in pharmaceutically acceptable salt form, in the preparation of a medicament or nutritional formulation for a combined use with an immunosuppressant or immunomodulating agent or a mixture thereof, in a method as defined hereinafter under 1.1 or 1.2;

4.1. A method of preventing or treating non TNF-induced transplant rejection in a recipient of organ or tissue transplant, e.g. heart, lung, combined heart-lung, trachea, liver, bowel, kidney or pancreatic transplants, comprising the step of administering to said recipient glycine, in free form or in pharmaceutically acceptable salt form, and an immunosuppressant or immunomodulating agent or a mixture thereof, in a therapeutically effective amount;

4.2. A method of preventing or treating manifestations of chronic rejection in a recipient of organ or tissue transplant, e.g. heart, lung, combined heart-lung, trachea, liver, bowel, kidney or pancreatic transplants, comprising the step of administering to said recipient glycine, in free form or in pharmaceutically acceptable salt form, and an immunosuppressant or immunomodulating agent or a mixture thereof, in a therapeutically effective amount;

5.1. A pharmaceutical composition or nutritional formulation for use in any method as defined hereinabove comprising glycine, in free form or in pharmaceutically acceptable salt form, in combination with an immunosuppressant or immunomodulating agent or a mixture thereof.

5.2. A kit or package for use in any method as defined hereinabove, said kit or package including a pharmaceutical composition or nutritional formulation comprising glycine in free form or in pharmaceutically acceptable salt form and a pharmaceutical composition comprising an immunosuppressant or immunomodulating agent, together with instructions to use.

According to a preferred embodiment of the invention, glycine is indicated optionally in combination with an immunosuppressant or immunomodulating agent for preventing or treating manifestations of chronic rejection.

According to the invention, glycine is conveniently employed in free amino acid form, in the form of glycine precursors, in particular alanine or serine, likewise in free amino acid form, in pharmaceutically acceptable salt form of said amino acids, or in form of mixtures of said amino acids and/or pharmaceutically acceptable salts thereof. Glycine is preferably used in free amino acid form, in pharmaceutically acceptable salt form or in the form of a mixture of glycine in free amino acid form with glycine in pharmaceutically acceptable salt form; most preferably glycine is in free amino acid form. Glycine may also be used in the form of a dipeptide according to the invention. Suitable salts include e.g. mineral or organic acid salts of the amino residue, and alkali or organic salts of the carboxylic acid residue.

Daily dosages of glycine required in treating or preventing diseases and conditions according to the invention will vary depending upon, for example, the host, the mode of administration, the severity of the condition to be treated and the optionally used (concomitantly, separately or in sequence) immunosuppressant or immunomodulating agent. A preferred daily dosage of glycine is about 1 to 80 g, preferably, 1 to 60 g, particularly preferred 15 to 30 g. It may also be administered to the patient in an amount such that its concentration in the patients'plasma is elevated to between 0.5 and 2.0 mM, preferably from 1.0 to 2.0 mM, although concentrations higher than this may be used. Suitable examples of immunosuppressants or immunomodulating agents include e.g. cyclosporins, rapamycins or ascomycins or their immunosuppressive analogs, e.g. Cyclosporin A, Cyclosporin G, FK-506, rapamycin, 40-O-(2-hydroxy) ethyl-rapamycin; corticosteroids; cyclophosphamide; azathioprine; methotrexate; brequinar; leflunomide; mizoribine; mycophenolic acid; mycophenolate mofetil; 15-deoxyspergualine; immunosuppressive antibodies, e.g. monoclonal antibodies to leukocyte receptors, e.g. MHC, CD2, CD3, CD4, CD7, CD25, CD28, B7, CD45, or CD 58 or their ligands; or other immunomodulatory compounds, e.e. CTLA4 lg.

Where glycine is administered in conjunction, i.e. sequentially, separately or concomitantly, with other immunosuppressive or immunomodulating therapy, e.g. as hereinabove specified, dosage of the co-administered immunosuppressant or immunomodulating agent will of course vary depending on the type of co-drug employed, e.g. whether it is a cyclosporin or an immunosuppressive antibody, on the specific drug employed, on the condition being treated, and so forth. According to the invention, glycine may also be administered in conjunction with a combination of immunosuppressants/immunomodulating agents, e.g. Cyclosporin A/ Steroids/Azathioprine or mycophenolate mofetil.

Glycine may be administered to the patient enterally or parenterally. The enteral administration route is preferred; particularly contemplated enteral administration routes are oral and/or tube feeding such as nasal feeding, particularly oral feeding. The medicament or nutritional formulation is conveniently administered in the form of an aqueous liquid. The medicament or nutritional formulation in a form suitable for enteral application is accordingly preferably aqueous or in powder form, whereby the powder is conveniently added to water prior to use. For use in tube feeding, the amount of water to be added will depend, inter alia, on the patients fluid requirements and condition. It will be appreciated that, for acute treatment, the parenteral application route is preferred.

When glycine is administered in the form of a medicament, it may be used together with pharmaceutically acceptable diluents or carriers, e.g. such for enteral or parenteral administration.

When glycine is administered in the form of a nutritional formulation, it may be used in combination with one or more of the following components: omega-3 polyunsaturated fatty acids, L-arginine or L-ornithine, a nucleobase source, e.g. a formulation as disclosed in U.S. Ser. No. 08/690476, the contents of which being herein incorporated by reference.

Glycine may also be administered in the form of a nutritional formulation which is a formula diet, e.g. a complete formula diet or preferably a diet supplement which can be administered over a long period of time. According to the invention formula diets may comprise, in addition to glycine, a source of carbohydrates, lipids fat (fat source), protein (nitrogen source) and optionally further nutritional components such as vitamins, minerals, trace elements and/or fibers (preferably soluble fibers), e.g. a formula diet as disclosed in US Ser. No. 08/690476, the contents of which being herein incorporated by reference. Preferably diet supplements for chronic administration comprise, in addition to glycine, a source of carbohydrates and further nutritional components such as vitamins, minerals, trace elements and flavoring agents and optionally arginine.

The medicament, diets and formulations of the invention may be obtained in a manner known per se, e.g. by admixing the ingredients.

Utility of glycine in treating or preventing diseases and conditions as hereinabove specified may be demonstrated in in vitro and in animal tests, for example with the methods described in the Examples.

The nutritional formulations of the invention are further illustrated by the Examples which are not intended in any way to limit the scope of the claimed invention.

EXAMPLE 1

Nutritional Formulations

TABLE 1

MM (Mineral Mix)

| Ingredients | g/100 g |
|---|---|
| Maltodextrins | 34.40 |
| K citrate/phosphate | 34.60 |
| Magnesium dicitrate | 8.20 |
| Calcium chloride | 8.00 |
| Sodium citrate/chloride | 9.00 |
| Citric acid | 3.50 |
| Choline tartrate | 2.30 |

TABLE 2

VM (Vitamin Mix)

| Ingredients | g/100 g |
|---|---|
| Maltodextrins | 43.44 |
| Sodium ascorbate | 35.00 |
| Vitamin E-Ac. 50% | 16.00 |
| Niacinamide | 1.55 |
| Vitamin A-Acetate | 1.20 |
| Ca-D-Panthothenat | 0.98 |
| Vitamin $K_1$ 1% | 0.71 |
| Vitamin $B_{12}$ 0.1% | 0.30 |
| Vitamin $D_3$ | 0.28 |
| Vitamin $B_6$ | 0.20 |
| Vitamin $B_1$ | 0.17 |
| Vitamin $B_2$ | 0.15 |
| Folic acid | 0.02 |
| Biotin | 0.01 |

TABLE 3

SM (Trace Elements)

| Ingredients | g/100 g |
|---|---|
| Maltodextrins | 47.79 |
| Molybdenum-yeast | 18.00 |
| Chromium-yeast | 9.20 |
| Zinc sulfate | 7.00 |
| Selenium-yeast | 7.00 |
| Ferrum(II) sulfate | 6.92 |
| Copper(II) gluconate | 2.24 |
| Manganese(II) sulfate | 1.12 |
| Sodium fluoride | 0.70 |
| Potassium iodide | 0.03 |

TABLE 4

Composition I Comprising Glycine

| Ingredients | g/100 g |
|---|---|
| Water | 77.40 |
| Maltodextrins | 12.28 |
| Na/Ca caseinates | 4.60 |
| Glycine | 3.00 |
| Lipids: | |
| Palm oil | 2.33 |
| Sunflower oil | 0.26 |
| Emulsifier Nathin E | 0.13 |
| | 100.00 |

TABLE 5

Composition II Comprising Glycine

| Ingredients | g/100 g |
|---|---|
| Water | 77.40 |
| Maltodextrins | 10.10 |
| Na/Ca caseinates | 4.60 |
| Glycine | 3.00 |
| MM | 2.00 |
| SM | 0.05 |
| VM | 0.10 |
| β-Carotine | 0.03 |
| Lipids: | |
| Palm oil | 2.33 |
| Sunflower oil | 0.26 |
| Emulsifier Nathin E | 0.13 |
| | 100.00 |

TABLE 6

Composition III Comprising Glycine (in powder form)

| Ingredients | g/100 g |
|---|---|
| Sugar | 59.163 |
| Glycine | 33.333 |
| Sodium citrate/chloride | 3.333 |
| Citric acid | 2.889 |
| Potassium chloride | 0.444 |
| Fresh flavour | 0.307 |
| Maltodextrins | 0.296 |
| Vitamin C | 0.129 |
| Magnesium carbonate | 0.053 |
| Calcium phosphate | 0.033 |
| Vitamin E-Ac. 50% | 2.000 |
| | 100.000 |

TABLE 7

Composition I Comprising Glycine and Arginine

| Ingredients | g/100 g |
|---|---|
| Water | 77.40 |
| Maltodextrins | 8.93 |
| Na/Ca caseinates | 4.60 |
| Glycine | 3.00 |
| Arginine | 1.17 |
| MM | 2.00 |
| SM | 0.05 |
| VM | 0.10 |
| β-Carotine | 0.03 |
| Lipids: | |
| Palm oil | 2.36 |
| Sunflower oil | 0.23 |
| Emulsifier Nathin E | 0.13 |
| | 100.00 |

TABLE 8

Composition II Comprising Glycine and Arginine (in powder form)

| Ingredients | g/100 g |
|---|---|
| Sugar | 59.937 |
| Glycine | 25.000 |
| Arginine | 15.833 |
| Sodium citrate/chloride | 2.499 |
| Citric acid | 1.667 |
| Potassium chloride | 0.333 |
| Fresh flavour | 0.333 |
| Maltodextrins | 0.221 |
| Vitamin C | 0.097 |
| Magnesium carbonate | 4.000 |
| Calcium phosphate | 2.500 |
| Vitamin E-Ac. 50% | 1.500 |
| | 100.000 |

TABLE 9

Composition Comprising Glycine and Fish Oil (ω-3 fatty acids)

| Ingredients | g/100 g |
|---|---|
| Water | 77.40 |
| Maltodextrins | 10.10 |
| Na/Ca caseinates | 4.60 |
| Glycine | 3.00 |
| MM | 2.00 |
| SM | 0.05 |
| VM | 0.10 |
| β-Carotine | 0.03 |
| Lipids: | |
| Palm oil | 1.32 |
| Sunflower oil | 0.23 |
| Emulsifier Nathin E | 0.13 |
| Fish Oil EPAX 3000 TG | 1.04 |
| | 100.00 |

EXAMPLE 2

The Effect of Dietary Glycine on Chronic Rejection in a Rat Aortic Transplant Model Orthotopic aortic transplantation between F-344 rats (donor) and Lewis rats (recipient) are completed across minor histocompatibility barriers. Recipients are fed control diet or glycine-containing diet (5%, w/w) for three days before transplantation. Rats are maintained on the same diets until sacrifice 6 or 8 weeks after transplantation. Grafts are removed and a portion is frozen or fixed in formalin for evaluation. Area of the four regions of the cross section of the aorta (lumen, intima, media and adventitia) are determined for each allograft. In cross sections of aortic allografts, intima proliferation (thickening), media necrosis (thinning) and infiltration of the adventitia (perivascular inflammation) are observed in all grafts regardless of diet. These features are typical of chronic rejection in the aortic transplant model, comparable to graft arteriosclerosis in human transplants. Aortic allografts from glycine fed recipients have decreased medial necrosis (in allografts of rats fed control diet, the medial area is reduced significantly to $1.5 \pm 0.3 \times 10^5$ μm$^2$, $p<0.05$, in contrast to medial areas of allografts from glycine fed rats, $3.5 \pm 0.2 \times 10^5$ μm$^2$, $p<0.05$, or medial areas of untransplanted abdominal aortas of Fisher-344 rats $3.3 \pm 0.3 \times 10^5$ μm$^2$, $p<0.05$) and a reduced perivascular inflammation (reduced number of infiltrating leukocytes in allograft adventita: $202 \pm 18$ vs. $140 \pm 13$, $p<0.05$). Dietary glycine increased the luminal area of a transplanted aorta significantly to $5.9\pm0.7$ vs. $3.6+0.2\times10^5$ $\mu m^2$, $p<0.05$ in comparison to a non-transplanted aorta. In addition, dietary glycine significantly reduced the ratio of intimal to medial area in the transplanted aorta to $0.45\pm0.15$ vs. $1.75\pm0.4$, $p<0.05$ the recipients receiving control diet.

What is claimed is:

1. A method of preventing or treating non TNF-induced transplant rejection in a recipient of organ or tissue transplant, comprising the step of enterally administering to said recipient a therapeutically effective amount of glycine, in free form or in pharmaceutically acceptable salt form.

2. A method of preventing or treating manifestations of chronic rejection in a recipient of organ or tissue transplant, comprising the step of enterally administering to said recipient a therapeutically effective amount of glycine, in free form or in pharmaceutically acceptable salt form.

3. The method according to claim 1 or wherein glycine is administered concomitantly, separately or sequentially with an immunosuppressant or an immunomodulating agent or a mixture thereof.

4. The method according to claim 2 wherein glycine is administered concomitantly, separately or sequentially with an immunosuppressant or an immunomodulating agent or a mixture thereof.

* * * * *